(12) United States Patent
Metzger et al.

(10) Patent No.: US 8,323,290 B2
(45) Date of Patent: Dec. 4, 2012

(54) TENSOR FOR USE IN SURGICAL NAVIGATION

(75) Inventors: Robert Metzger, Wakarusa, IN (US); Ryan Cameron Lakin, Newton, NJ (US)

(73) Assignee: Biomet Manufacturing Corp., Warsaw, IN (US)

( * ) Notice: Subject to any disclaimer, the term of this patent is extended or adjusted under 35 U.S.C. 154(b) by 1271 days.

(21) Appl. No.: 11/681,227

(22) Filed: Mar. 2, 2007

(65) Prior Publication Data

US 2007/0244488 A1 Oct. 18, 2007

Related U.S. Application Data

(60) Provisional application No. 60/778,709, filed on Mar. 3, 2006.

(51) Int. Cl.
*A61B 17/66* (2006.01)
(52) U.S. Cl. .......................................... 606/90
(58) Field of Classification Search ............... 600/424; 606/90, 87–89, 86 R, 102
See application file for complete search history.

(56) References Cited

U.S. PATENT DOCUMENTS

| | | | |
|---|---|---|---|
| 4,341,220 A | 7/1982 | Perry | |
| 4,360,028 A | 11/1982 | Barbier et al. | |
| 4,501,266 A * | 2/1985 | McDaniel | 606/90 |
| 5,213,112 A * | 5/1993 | Niwa et al. | 600/587 |
| 5,309,913 A | 5/1994 | Kormos et al. | |
| 5,517,990 A | 5/1996 | Kalfas et al. | |
| 5,611,353 A * | 3/1997 | Dance et al. | 600/595 |
| 5,628,315 A | 5/1997 | Vilsmeier et al. | |
| 5,669,914 A * | 9/1997 | Eckhoff | 606/88 |
| 5,688,282 A * | 11/1997 | Baron et al. | 606/90 |
| 5,732,703 A | 3/1998 | Kalfas et al. | |
| 5,769,861 A | 6/1998 | Vilsmeier | |
| 5,776,064 A | 7/1998 | Kalfas et al. | |
| 5,911,723 A * | 6/1999 | Ashby et al. | 606/88 |
| 5,967,982 A | 10/1999 | Barnett | |
| 5,980,535 A | 11/1999 | Barnett et al. | |
| 5,999,837 A | 12/1999 | Messner et al. | |
| 6,021,343 A | 2/2000 | Foley et al. | |
| 6,122,541 A | 9/2000 | Cosman et al. | |
| 6,190,395 B1 | 2/2001 | Williams | |
| 6,226,548 B1 | 5/2001 | Foley et al. | |
| 6,236,875 B1 * | 5/2001 | Bucholz et al. | 600/407 |
| 6,340,363 B1 | 1/2002 | Bolger et al. | |
| 6,348,058 B1 | 2/2002 | Melkent et al. | |
| 6,377,839 B1 | 4/2002 | Kalfas et al. | |
| 6,385,475 B1 * | 5/2002 | Cinquin et al. | 600/407 |
| 6,434,507 B1 | 8/2002 | Clayton et al. | |
| 6,471,706 B1 | 10/2002 | Schumacher et al. | |
| 6,490,467 B1 | 12/2002 | Bucholz et al. | |
| 6,697,664 B2 | 2/2004 | Kienzle, III et al. | |
| 6,725,080 B2 | 4/2004 | Melkent et al. | |
| 6,796,988 B2 | 9/2004 | Melkent et al. | |
| 6,856,828 B2 | 2/2005 | Cossette et al. | |

(Continued)

*Primary Examiner* — Kevin T Truong
*Assistant Examiner* — Christopher Beccia
(74) *Attorney, Agent, or Firm* — Ryan O. White, Esq.; Taft Stettinius & Hollister LLP

(57) ABSTRACT

A tensor for use with a surgical navigation system is provided. The tensor comprises a first bone engaging member engageable with a first bone and a second bone engaging member engageable with a second bone. A force-applying mechanism is configured to forcibly move the first and second bone engaging members relative to one another and a sensor detects the value of the force applied by the force-applying mechanism. A transmitter communicates a parameter associated with the tensor to the surgical navigation system.

23 Claims, 14 Drawing Sheets

U.S. PATENT DOCUMENTS

| | | | |
|---|---|---|---|
| 6,859,661 B2 * | 2/2005 | Tuke | 600/424 |
| 6,887,245 B2 | 5/2005 | Kienzle, III et al. | |
| 6,887,247 B1 | 5/2005 | Couture et al. | |
| 6,899,714 B2 | 5/2005 | Vaughan | |
| 6,923,817 B2 | 8/2005 | Carson et al. | |
| 6,932,823 B2 | 8/2005 | Grimm et al. | |
| 6,980,849 B2 | 12/2005 | Sasso | |
| 7,008,430 B2 | 3/2006 | Dong et al. | |
| 7,686,812 B2 * | 3/2010 | Axelson et al. | 606/88 |
| 7,686,813 B2 * | 3/2010 | Stutz et al. | 606/90 |
| 7,763,020 B2 * | 7/2010 | Draper | 606/59 |
| 7,840,256 B2 * | 11/2010 | Lakin et al. | 600/426 |
| 2002/0095081 A1 | 7/2002 | Vilsmeier | |
| 2003/0069591 A1 | 4/2003 | Carson et al. | |
| 2004/0102785 A1 | 5/2004 | Hodorek et al. | |
| 2004/0249314 A1 * | 12/2004 | Salla et al. | 600/595 |
| 2004/0267242 A1 | 12/2004 | Grimm et al. | |
| 2005/0015005 A1 | 1/2005 | Kockro | |
| 2005/0020941 A1 * | 1/2005 | Tarabichi | 600/587 |
| 2005/0021031 A1 | 1/2005 | Foley et al. | |
| 2005/0021037 A1 | 1/2005 | McCombs et al. | |
| 2005/0021039 A1 | 1/2005 | Cusick et al. | |
| 2005/0038432 A1 | 2/2005 | Shaolian et al. | |
| 2005/0038514 A1 | 2/2005 | Helm et al. | |
| 2005/0049485 A1 | 3/2005 | Harmon et al. | |
| 2005/0059885 A1 | 3/2005 | Melkent et al. | |
| 2005/0070900 A1 | 3/2005 | Serhan et al. | |
| 2005/0075632 A1 | 4/2005 | Russell et al. | |
| 2005/0080334 A1 | 4/2005 | Willis | |
| 2005/0101966 A1 | 5/2005 | Lavallee | |
| 2005/0113659 A1 | 5/2005 | Pothier et al. | |
| 2005/0113846 A1 | 5/2005 | Carson | |
| 2005/0119661 A1 | 6/2005 | Hodgson et al. | |
| 2005/0119783 A1 | 6/2005 | Brisson et al. | |
| 2005/0177169 A1 | 8/2005 | Fisher et al. | |
| 2005/0177170 A1 | 8/2005 | Fisher et al. | |
| 2005/0215888 A1 | 9/2005 | Grimm et al. | |
| 2005/0234332 A1 | 10/2005 | Murphy | |
| 2005/0234461 A1 | 10/2005 | Burdulis, Jr. et al. | |
| 2005/0234465 A1 | 10/2005 | McCombs et al. | |
| 2005/0234468 A1 * | 10/2005 | Carson | 606/96 |
| 2005/0251065 A1 | 11/2005 | Henning et al. | |
| 2005/0251148 A1 | 11/2005 | Friedrich et al. | |
| 2005/0261680 A1 * | 11/2005 | Draper | 606/59 |
| 2005/0267353 A1 | 12/2005 | Marquart et al. | |
| 2005/0267354 A1 | 12/2005 | Marquart et al. | |
| 2005/0267358 A1 | 12/2005 | Tuma et al. | |
| 2005/0267485 A1 | 12/2005 | Cordes et al. | |
| 2006/0009778 A1 | 1/2006 | Collins et al. | |
| 2006/0015018 A1 | 1/2006 | Jutras et al. | |
| 2006/0015031 A1 * | 1/2006 | Kienzle | 600/424 |
| 2006/0015120 A1 | 1/2006 | Richard et al. | |
| 2006/0052691 A1 | 3/2006 | Hall et al. | |
| 2006/0241569 A1 * | 10/2006 | DiSilvestro | 606/1 |
| 2007/0225595 A1 * | 9/2007 | Malackowski et al. | 600/424 |
| 2007/0233144 A1 * | 10/2007 | Lavallee et al. | 606/90 |

* cited by examiner

TENSOR FOR USE IN SURGICAL NAVIGATION

CROSS-REFERENCE TO RELATED APPLICATIONS

This application claims the benefit of U.S. Provisional Patent Application Ser. No. 60/778,709, filed Mar. 3, 2006, which is incorporated in its entirety herein by this reference.

FIELD OF THE INVENTION

The present teachings relate generally to surgical navigation and more particularly to a tensor and methods of using the tensor to balance ligaments or to distract bones during a surgical navigation procedure.

BACKGROUND

Surgical navigation systems, also known as computer assisted surgery and image guided surgery, aid surgeons in locating patient anatomical structures, guiding surgical instruments, and implanting medical devices with a high degree of accuracy. Surgical navigation has been compared to a global positioning system that aids vehicle operators to navigate the earth. A surgical navigation system typically includes a computer, a tracking system, and patient anatomical information. The patient anatomical information can be obtained by using an imaging mode such as fluoroscopy, computer tomography (CT) or by simply defining the location of patient anatomy with the surgical navigation system. Surgical navigation systems can be used for a wide variety of surgeries to improve patient outcomes.

To successfully implant a medical device, surgical navigation systems often employ various forms of computing technology, as well as utilize intelligent instruments, digital touch devices, and advanced 3-D visualization software programs. All of these components enable surgeons to perform a wide variety of standard and minimally invasive surgical procedures and techniques. Moreover, these systems allow surgeons to more accurately plan, track and navigate the placement of instruments and implants relative to a patient's body, as well as conduct pre-operative and intra-operative body imaging.

To accomplish the accurate planning, tracking and navigation of surgical instruments, tools and/or medical devices during a surgical procedure utilizing surgical navigation, surgeons often use "tracking arrays" that are coupled to the surgical components. The tracking arrays allow the surgeon to accurately track the location of these surgical components, as well as the patient's bones during the surgery. By knowing the physical location of the tracking array, the software detection program of the tracking system is able to calculate the position of the tracked component relative to a surgical plan image.

In a total knee arthroplasty ("TKA") procedure to replace a worn or damaged knee, a significant amount of effort is devoted to ensuring that the resulting knee joint will be balanced. This balancing procedure is referred to as "soft tissue balancing." Balancing may involve releasing the medial or collateral ligaments to correct for a varus or valgus deformity, such that the anatomical axis of the knee is correct when equal forces are applied to both collateral ligaments. A balanced knee joint will demonstrate proper ligament tension through the full range of motion, which provides a natural acting joint and minimizes pain and discomfort. Further, properly balanced ligaments reduce stress, wear and tear on the prosthesis and extend its life.

Soft tissue balancing is an imprecise art because there are few ways to precisely quantify the true tension of the ligaments, and this is further complicated by the pathology of arthritis. The amount of true contracture of the knee ligaments and the associated amount of soft tissue releasing required to obtain a "balanced" knee is often uncertain. It is known to use various distraction or "tensor" devices that have members that push the tibia apart from the femoral condyles with a known or pre-determined force, thereby applying the known force to the collateral ligaments. These tensors are often applied only after the bone cuts are complete, however, and are thus used as no more than a check on bone cuts that have been made from standard resection procedures.

Soft tissue balancing represents one of the major unsolved problems in knee surgery, and there is considerable interest in developing tools to assist with this process, especially in surgical navigation procedures.

SUMMARY OF THE INVENTION

The present teachings provide an apparatus and method of ligament balancing or bone distraction during a surgical navigation procedure.

In one form thereof, there is provided a tensor for use with a surgical navigation system. The tensor comprises a first bone engaging member engageable with a first bone and a second bone engaging member engageable with a second bone. A force-applying mechanism configured to forcibly move the first and second bone engaging members relative to one another and a sensor detects the value of the force applied by the force-applying mechanism. A transmitter communicates a parameter associated with by the tensor to the surgical navigation system.

BRIEF DESCRIPTION OF DRAWINGS

The above-mentioned aspects of the present teachings and the manner of obtaining them will become more apparent and the teachings will be better understood by reference to the following description of the embodiments taken in conjunction with the accompanying drawings, wherein.

Corresponding reference characters indicate corresponding parts throughout the several views.

DETAILED DESCRIPTION

The embodiments of the present teachings described below are not intended to be exhaustive or to limit the invention to the precise forms disclosed in the following detailed description. Rather, the embodiments are chosen and described so that others skilled in the art may appreciate and understand the principles and practices of the present teachings.

Figure 1:
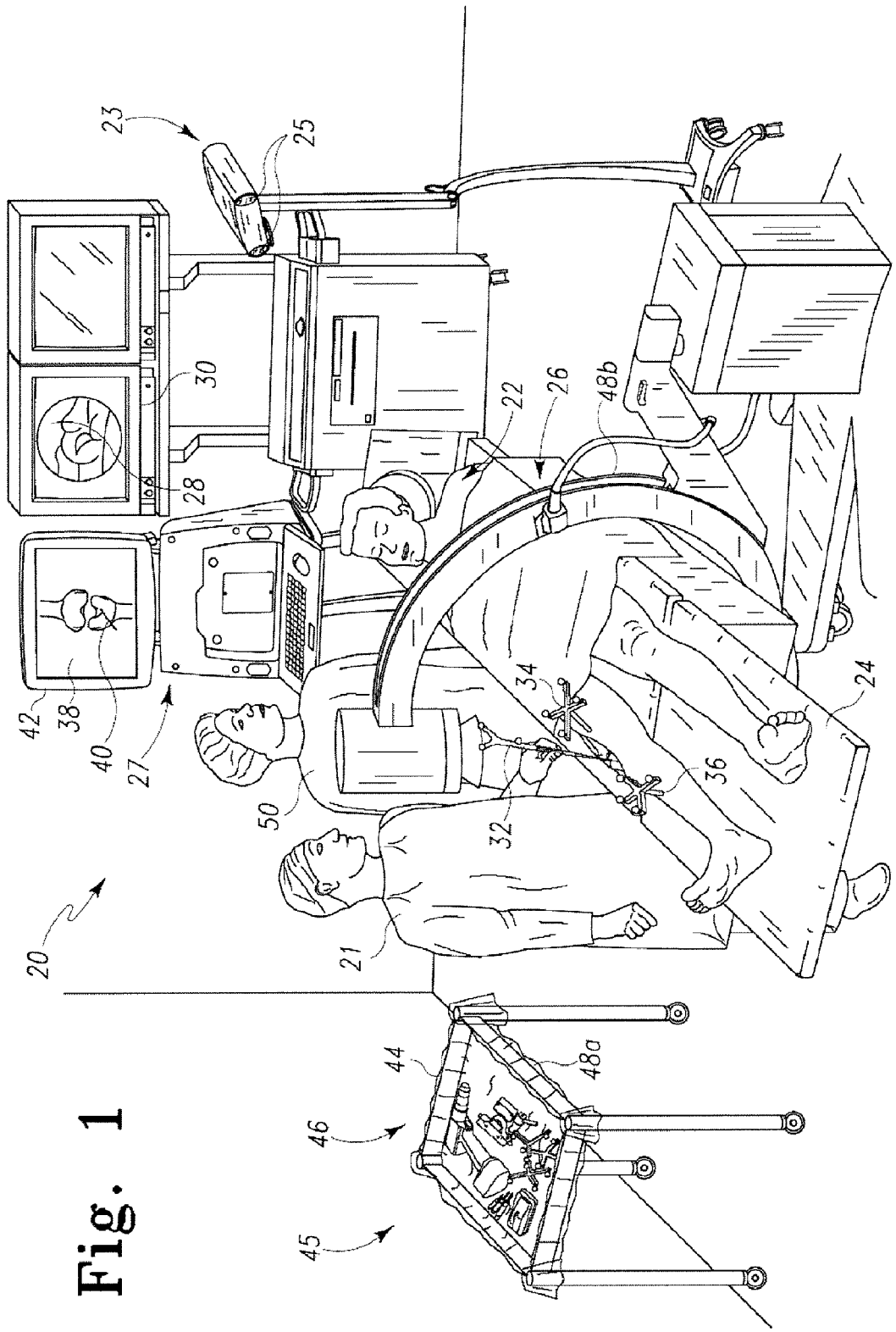
FIG. 1 is a perspective view of an exemplary operating room setup in a surgical navigation embodiment in accordance with the present teachings.

FIG. 1 shows a perspective view of an operating room with surgical navigation system 20. Surgeon 21 is aided by the surgical navigation system in performing knee arthroplasty, also known as knee replacement surgery, on patient 22 shown lying on operating table 24. Surgical navigation system 20 has a tracking system that locates arrays and tracks them in real-time. To accomplish this, the surgical navigation system includes optical locator 23, which has two CCD (charge couple device) cameras 25 that detect the positions of the arrays in space by using triangulation methods. The relative location of the tracked arrays, including the patient's anatomy, can then be shown on a computer display (such as computer display 27 for instance) to assist the surgeon during the surgical procedure. The arrays that are typically used include probe arrays, instrument arrays, reference arrays, and calibrator arrays. The operating room includes an imaging system such as C-arm fluoroscope 26 with fluoroscope display image 28 to show a real-time image of the patient's knee on monitor 30. Surgeon 21 uses surgical probe 32 to reference a point on the patient's knee, and reference arrays 34, 36 attached to the patient's femur and tibia to provide known anatomic reference points so the surgical navigation system can compensate for leg movement. The relative location of probe array 32 to the patient's tibia is then shown as reference numeral 40 on computer display image 38 of computer monitor 42. The operating room also includes instrument cart 45 having tray 44 for holding a variety of surgical instruments and arrays 46. Instrument cart 45 and C-arm 26 are typically draped in sterile covers 48a, 48b to eliminate contamination risks within the sterile field.

The surgery is performed within a sterile field, adhering to the principles of asepsis by all scrubbed persons in the operating room. Patient 22, surgeon 21 and assisting clinician 50 are prepared for the sterile field through appropriate scrubbing and clothing. The sterile field will typically extend from operating table 24 upward in the operating room. Typically both computer display image 38 and fluoroscope display image 28 are located outside of the sterile field.

A representation of the patient's anatomy can be acquired with an imaging system, a virtual image, a morphed image, or a combination of imaging techniques. The imaging system can be any system capable of producing images that represent the patient s anatomy such as a fluoroscope producing x-ray two-dimensional images, computer tomography (CT) producing a three-dimensional image, magnetic resonance imaging (MRI) producing a three-dimensional image, ultrasound imaging producing a two-dimensional image, and the like. A virtual image of the patient's anatomy can be created by defining anatomical points with surgical navigation system 20 or by applying a statistical anatomical model. A morphed image of the patient's anatomy can be created by combining an image of the patient's anatomy with a data set, such as a virtual image of the patient's anatomy. Some imaging systems, such as C-arm fluoroscope 26, can require calibration. The C-arm can be calibrated with a calibration grid that enables determination of fluoroscope projection parameters for different orientations of the C-arm to reduce distortion. A registration phantom can also be used with a C-arm to coordinate images with the surgical navigation application program and improve scaling through the registration of the C-arm with the surgical navigation system. A more detailed description of a C-aim based navigation system is provided in James B. Stiehl et al., Navigation and Robotics in Total Joint and Spine Surgery, Chapter 3 C-Arm-Based Navigation, Springer-Verlag (2004).

Figure 2:
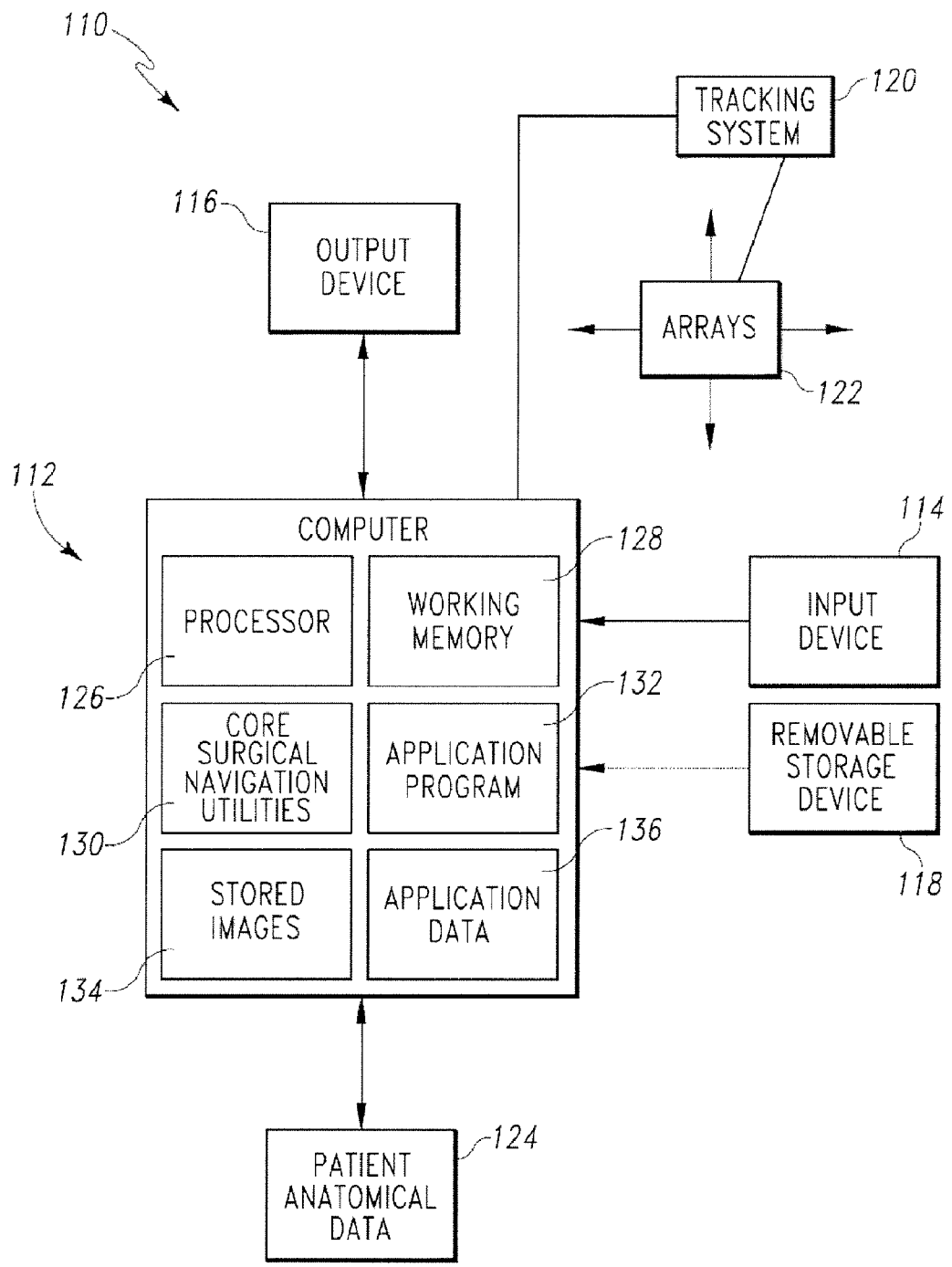
FIG. 2 is an exemplary block diagram of a surgical navigation system embodiment in accordance with the present teachings.

FIG. 2 is a block diagram of an exemplary surgical navigation system embodiment in accordance with the present teachings, such as an Acumen™ Surgical Navigation System available from EBI, L.P., Parsipaimy, N.J. USA, a Biomet Company. The surgical navigation system 110 comprises computer 112, input device 114, output device 116, removable storage device 118, tracking system 120, arrays 122, and patient anatomical data 124, as further described in the brochure Acumen™ Surgical Navigation System, Understanding Surgical Navigation (2003), available from EBI, L.P. The Acumen™ Surgical Navigation System can operate in a variety of imaging modes such as a fluoroscopy mode creating a two-dimensional x-ray image, a computer-tomography (CT) mode creating a three-dimensional image, and an imageless mode creating a virtual image or planes and axes by defining anatomical points of the patient's anatomy. In the imageless mode, a separate imaging device such as a C-arm is not required, thereby simplifying set-up. The Acumen™ Surgical Navigation System can run a variety of orthopedic applications, including applications for knee arthroplasty, hip arthroplasty, spine surgery, and trauma surgery, as further described in the brochure "Acumen™ Surgical Navigation System, Surgical Navigation Applications" (2003) available from EBI, L.P. A more detailed description of an exemplary surgical navigation system is provided in James B. Stiehl et al., Navigation and Robotics in Total Joint and Spine Surgery, Chapter 1 Basics of Computer-Assisted Orthopedic Surgery (CAOS), Springer-Verlag (2004).

Computer 112 can be any computer capable of properly operating surgical navigation devices and software, such as a computer similar to a commercially available personal computer that comprises a processor 126, working memory 128, core surgical navigation utilities 130, an application program 132, stored images 134, and application data 136. Processor 126 is a processor of sufficient power for computer 112 to perform desired functions, such as one or more microprocessors. Working memory 128 is memory sufficient for computer 112 to perform desired functions such as solid-state memory, random-access memory, and the like. Core surgical navigation utilities 130 are the basic operating programs, and include image registration, image acquisition, location algorithms, orientation algorithms, virtual keypad, diagnostics, and the like. Application program 132 can be any program configured for a specific surgical navigation purpose, such as orthopedic application programs for unicondylar knee ("uni-kee"), total knee, hip, spine, trauma, intramedullary ("IM") nail, and external fixator. Stored images 134 are those recorded during image acquisition using any of the imaging systems previously discussed. Application data 136 is data that is generated or used by application program 132, such as implant geometries, instrument geometries, surgical defaults, patient landmarks, and the like. Application data 136 can be pre-loaded in the software or input by the user during a surgical navigation procedure.

Output device 116 can be any device capable of creating an output useful for surgery, such as a visual output and an auditory output. The visual output device can be any device capable of creating a visual output useful for surgery, such as a two-dimensional image, a three-dimensional image, a holographic image, and the like. The visual output device can be a monitor for producing two and three-dimensional images, a projector for producing two and three-dimensional images, and indicator lights. The auditory output can be any device capable of creating an auditory output used for surgery, such as a speaker that can be used to provide a voice or tone output.

Removable storage device 118 can be any device having a removable storage media that would allow downloading data such as application data 136 and patient anatomical data 124. The removable storage device can be a read-write compact disc (CD) drive, a read-write digital video disc (DVD) drive, a flash solid-state memory port, a removable hard drive, a floppy disc drive, and the like.

Tracking system 120 can be any system that can determine the three-dimensional location of devices carrying or incorporating markers that serve as tracking indicia. An active tracking system has a collection of infrared light emitting diode (ILEDs) illuminators that surround the position sensor lenses to flood a measurement field of view with infrared light. A passive system incorporates retro-reflective markers that reflect infrared light back to the position sensor, and the system triangulates the real-time position (x, y, and z location) and orientation (rotation around x, y, and z axes) of an array 122 and reports the result to the computer system with an accuracy of about 0.35 mm Root Mean Squared (RMS). An example of passive tracking system is a Polaris® Passive System and an example of a marker is the NDI Passive Spheres™ both available from Northern Digital Inc. Ontario, Canada. A hybrid tracking system can detect active and active wireless markers in addition to passive markers. Active marker based instruments enable automatic tool identification, program control of visible LEDs, and input via tool buttons. An example of a hybrid tracking system is the Polaris® Hybrid System available from Northern Digital Inc. A marker can be a passive IR reflector, an active IR emitter, an electromagnetic marker, and an optical marker used with an optical camera.

As is generally known within the art, implants and instruments may also be tracked by electromagnetic tracking systems. These systems locate and track devices and produce a real-time, three-dimensional video display of the surgical procedure. This is accomplished by using electromagnetic field transmitters that generate a local magnetic field around the patient's anatomy. In turn, the localization system includes magnetic sensors that identify the position of tracked instruments as they move relative to the patient's anatomy. By not requiring a line of sight with the transmitter, electromagnetic systems are also adapted for in vivo use, and are also integrable, for instance, with ultrasound and CT imaging processes for performing interventional procedures by incorporating miniaturized tracking sensors into surgical instruments. By processing transmitted signals generated by the tracking sensors, the system is able to determine the position of the surgical instruments in space, as well as superimpose their relative positions onto pre-operatively captured CT images of the patient.

Arrays 122 can be probe arrays, instrument arrays, reference arrays, calibrator arrays, and the like. Arrays 122 can have any number of markers, but typically have three or more markers to define real-time position (x, y, and z location) and orientation (rotation around x, y, and z axes). As will be explained in greater detail below, an array comprises a body and markers. The body comprises an area for spatial separation of markers. In some embodiments, there are at least two arms and some embodiments can have three arms, four arms, or more. The arms are typically arranged asymmetrically to facilitate specific array and marker identification by the tracking system. In other embodiments, such as a calibrator array, the body provides sufficient area for spatial separation of markers without the need for arms. Arrays can be disposable or non-disposable. Disposable arrays are typically manufactured from plastic and include installed markers. Non-disposable arrays are manufactured from a material that can be sterilized, such as aluminum, stainless steel, and the like. The markers are removable, so they can be removed before sterilization.

Planning and collecting patient anatomical data 124 is a process by which a clinician inputs into the surgical navigation system actual or approximate anatomical data. Anatomical data can be obtained through techniques such as anatomic painting, bone morphing, CT data input, and other inputs, such as ultrasound and fluoroscope and other imaging systems.

Figure 3:
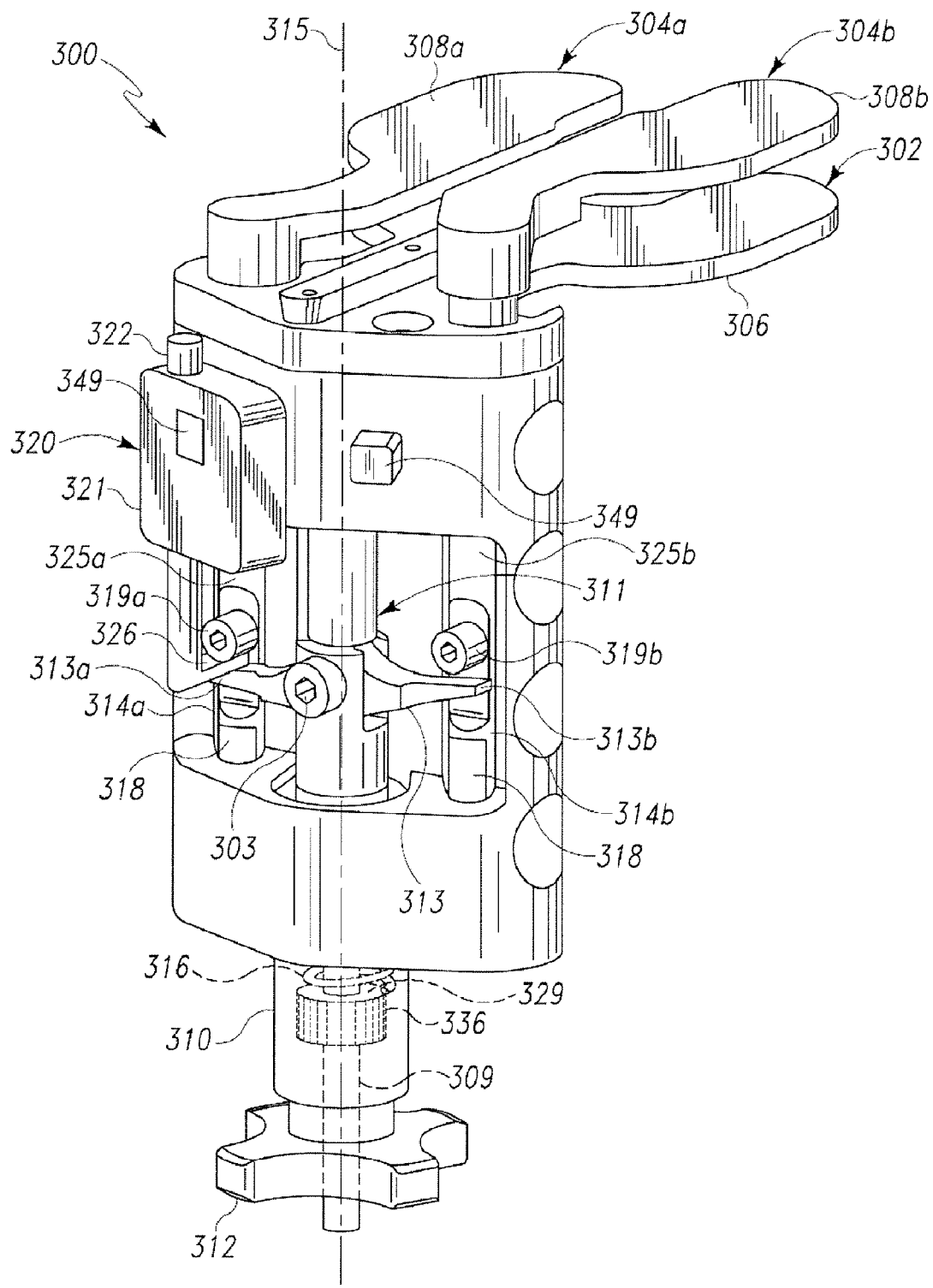
FIG. 3 is a perspective view of an exemplary tensor device in accordance with the present teachings.
Figure 4:
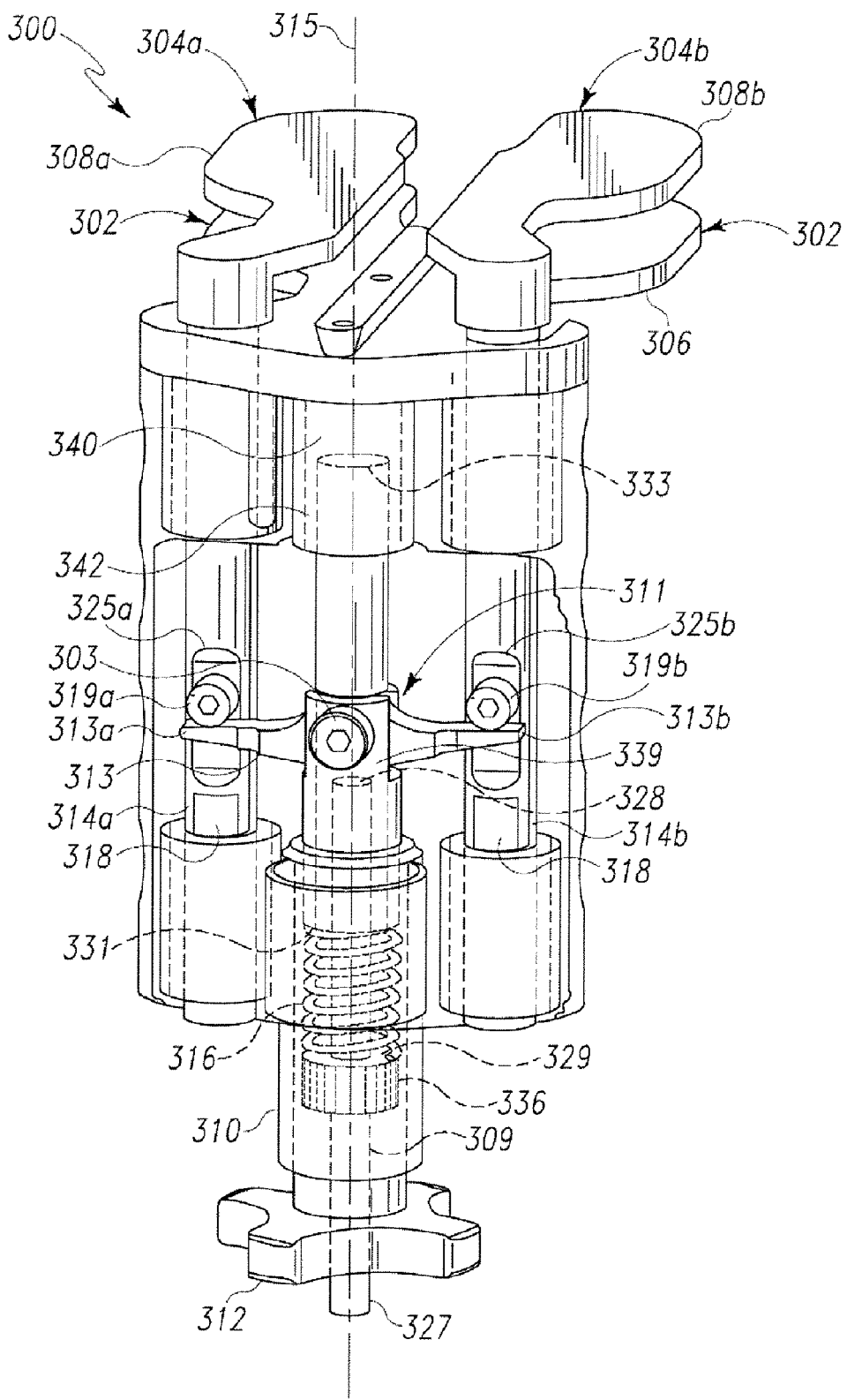
FIG. 4 is a partial phantom view of the exemplary tensor of FIG. 3.

FIGS. 3 and 4 illustrate an exemplary knee distraction device or tensor 300 for use with surgical navigation system 20. Tensor 300 includes a first bone engaging member 302 and a pair of second bone engaging members 304a, 304b, which are vertically adjustable relative to one another and to member 302. To achieve this vertical movement, bone engaging members 304a, 304b are respectively coupled to outer shafts 314a, 314b, which are movable along vertical axis 315. Outer shafts 314a, 314b each include an extension peg 319a, 319b that extends horizontally away from its front surface 325a, 325b, respectively, and is positioned adjacent to and substantially on top of ends 313a, 313b of pivot arm 313. Pivot arm 313 extends outwardly from shaft 311 and is configured to pivot upwardly or downwardly relative to central peg 303 much like a seesaw structure pivoting about a central fulcrum point.

The mechanism for forcibly adjusting members 302 and 304a, 304b vertically apart from one another is by means of rod 309, shaft 311, load cell 336 and spring 316. Rod 309 is housed in tubular member 310 and is fixably attached to operating knob or dial 312 near its distal end 327. Proximal end 328 of rod 309 is housed inside of central bore 339 of shaft 311 and is configured to move upwardly relative to the shaft. More particularly, rod 309 may advance into central bore 339 of shaft 311, as described in more detail below. Load cell 336 is fixably coupled to rod 309 and includes an upper surface 329 to support spring 316. Spring 316 surrounds rod 309 and is positioned between upper surface 329 of load cell 336 and bottom surface 331 of the shaft 311, to which it is keyed.

Figure 5:
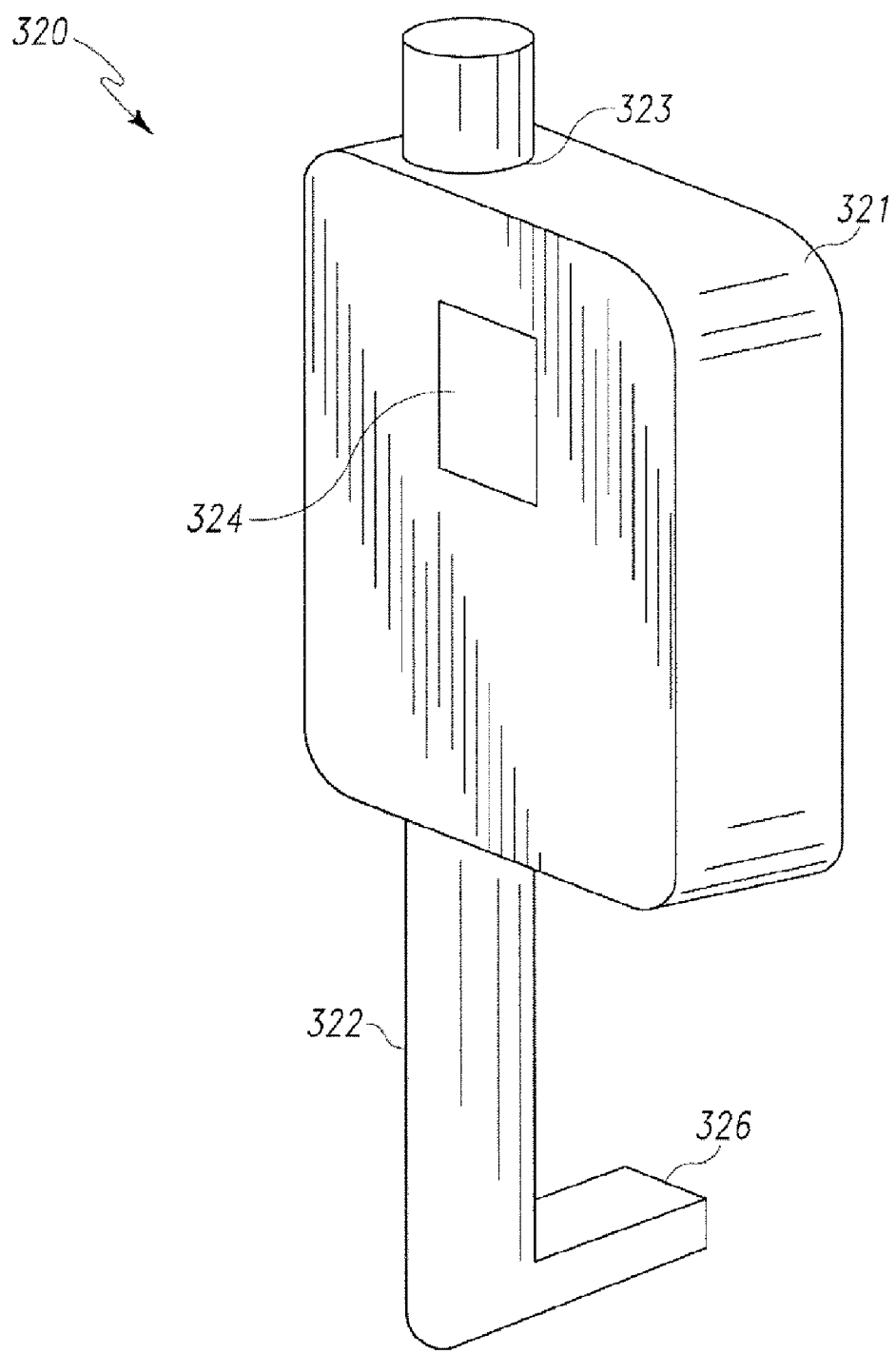
FIG. 5 is a perspective view of an exemplary communication device in accordance with the present teachings.

Tensor 300 further includes a removable and autoclavable transmitter 320 (best shown in FIG. 5), which detects and transmits the value of force applied to bone engaging members 304a, 304b at any give time to the computer of the navigation system. Transmitter 320 includes a body 321, attachment port 324 for connecting the transmitter to the tensor at one of attachment pegs 349, and attachment arm 322, which is configured to move relative to body 321 by way of internal bore 323. Body 321 houses the internal sensing circuitry of the transmitter which is configured to detect and measure distraction forces. In one exemplary embodiment, transmitter 320 further comprises a sensor, such as a transducer device that is configured to detect the value of force applied by the force-applying means of the tensor and transmit this force to the computer system. To measure the distraction force, attachment arm 322 has a sensing arm 326 that is sandwiched between the end 313a of pivot arm 313 and extension peg 319a. Sensing arm 326 is configured with a pressure sensitive material or film, such as FlexiForce® Load/Force Sensors and System manufactured by Tekscan, Inc., 307 West First Street. South Boston, Mass. 02127-1309, and capable of determining the pressure encountered by either one of bone engaging members 304a, 304b when they respectively contact soft tissue or bone during the distraction process. More particularly, when either one of the bone engaging members 304a, 304b comes into contact with soft tissue or bone during the distraction process, that engaging member will encounter resistance to upward movement. This resistance is then received by the respective outer shaft 314a, 314b which is connected to the engaging member that contacts the soft tissue or bone. As this resistance is received by the outer shaft, extension peg 319a is forced downward against sensing arm 326, which in turn contacts pivot arm 313. Because sensing arm 326 contains a pressure sensitive material, transmitter 320 is able to detect the distraction force and translate it into a pressure reading to be transmitted to the computer system via a communication link. In one exemplary embodiment according to the present teachings, transmitter 320 is an infrared transmitter device capable of establishing a communication link with the navigation system. Infrared transmission devices are known in the art and do not need to be discussed in further detail here.

In addition to transmitting the force exerted by the tensor device, transmitter 320 is also configured to measure and transmit the space between members 302 and 304a, 304b and/or the distance between the tibial plateau and the condyles during the distraction process. More particularly, as a downward force is exerted onto outer shaft 314a and ultimately onto pivot arm 313, the left side of the pivot arm pivots downwardly and correspondingly causes attachment arm 322 to displace downwardly relative to body 321 through the internal bore 323. This displacement is measured by the transmitter and then transmitted to the navigation system. Alternatively and/or additionally, the tensor is also adapted to comprise a gap or joint space indicator 318 on one or both of the outer shafts 314a, 314b. According to this embodiment, indicator 318 includes a visible indication screen (such as an LCD screen or other such display surface) which is located directly on the surface of the tensor and configured to display the distance between the tibial plateau and the condyles and/or the distance between the bone engaging members during the distraction process.

The remaining structural details of the tensor assembly of the illustrated embodiment can be better understood with reference to a description of operation. Returning now to FIGS. 3 and 4, when dial 312 is turned or rotated, rod 309 may advance upwardly along vertical axis 315 and further into central bore 339 of shaft 311. As will be explained in more detail below, the extent to which rod 309 advances into central bore 339 depends on the extent of the resistance bone engaging members 304a, 304b encounter from soft tissue or bone during the distraction process. If bone engaging members 304a, 304b are free to move upward without encountering significant resistance from either bone or soft tissue, rod 309 advances further into central bore 339. As this happens, load cell 336, which is fixably attached to rod 309, also moves upwardly along the vertical axis. Load cell 336 exerts a compressive force on spring 316 and causes it to upwardly bias the bottom portion 331 of shaft 311. As the upper surface 329 of load cell 336 exerts a force on spring 316, spring 316 may compress somewhat as it engages the bottom portion 331 of shaft 311. The amount spring 316 compresses will depend on the amount of resistance against upward movement provided by bone engaging members 304a, 304b during the distraction process. For instance, if bone engaging members 304a, 304b are free to move vertically upward before encountering resistance from either a bone or soft tissue, spring 316 may not compress at all or may only slightly compress. However, once either one of bone engaging members 304a, 304b encounters significant resistance from soft tissue or bone, spring 316 will compress in response to this resistance. This resistance is received by the corresponding outer shaft (314a, 314b) of the bone engaging member, which in turn forces the extension peg (319a or 319b) to press against or come into contact with the corresponding end portion (313a or 313b) of pivot arm 313. Moreover, spring 316 compresses and exerts a force against top surface 329 of load cell 336. In certain exemplary embodiments, load cell 336 is a wired or wireless load cell capable of calculating the exerted force and transmitting this value to the navigation system. Load cells are known within the art and do not need to be discussed in further detail here.

As rod 309 is advanced upwardly during the distraction process, the compressive force on spring 316 increases, resulting in load cell 336 moving closer to shaft 311 as the spring compresses and/or shaft 311 advances vertically upward. As shaft 311 advances vertically upward, its proximal end 333 advances further into bore 340 of upper housing 342. As described above, pivot arm 313 is pivotably mounted to shaft 311 and thus moves upwardly along with shaft 311. As this happens, the ends 313a and 313b of pivot arm exert upward forces on pegs 319a and 319b, respectively. However, the amount of resistance the ends encounter by pegs 319a and 319b at any given time depends upon the individual force encountered by bone engaging members 304a and 304b from the respective ligaments or bones being distracted. In practice, as the bone engaging members 304a, 304b first begin displacing away from member 302, they will likely not be touching their respective condyles and therefore will likely encounter little resistance, such that arm 311 will not significantly pivot about peg 319a as shaft 311 moves upwardly. Once the engaging members 304a, 304b begin to distract their respective ligaments, the end 313a or 313b that encounters the least resistance from its respective peg will move upwardly to a greater extent (i.e., arm 313 pivots) and thus displaces its respective engaging member (304a or 304b) to a greater extent until the amount of downward force on both ends 313a, 313b of arm 313 is the same.

Figure 6:
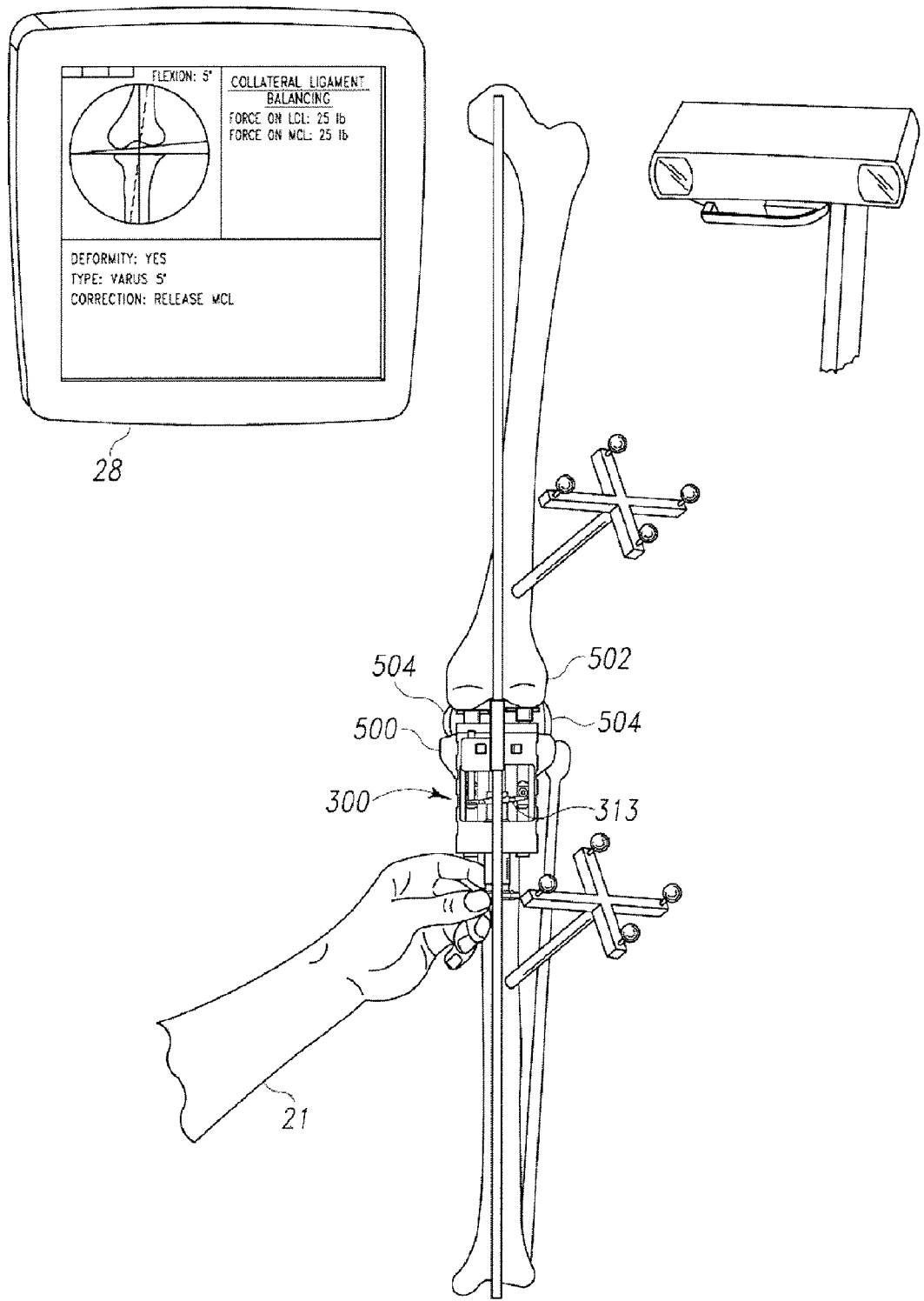
FIGS. 6-9 are fragmentary perspective views illustrating various steps of an exemplary tensor device being used in a surgical navigation knee procedure in accordance with the present teachings.

To better understand and appreciate the present teachings, an exemplary illustration of a knee distraction process is now provided. As is known in the art, a key to reinstating natural joint function involves alignment of the mechanical axis of the leg with the balanced tension on the collateral ligaments and related soft tissue. As shown in FIG. 6, tensor 300 is placed between tibia 500 and femur 502 of a knee with the leg in 5-10 degrees of flexion. More particularly, the bottom surface 306 of first bone engaging member 302 rests on the tibial plateau of the tibia while the upper surfaces 308a, 308b of the femoral condyle-engaging members 304a, 304b engage the respective condyles of the femur. Tension is applied with the leg in 5-10 degrees of flexion to ensure that tension is applied to the collaterals and not the posterior capsule. The surgeon 21 adjusts the tensor 300 to apply an equal amount of force (e.g., 20-30 lbs.) to both collateral ligaments 504 (i.e., medial and lateral). Pivot arm 313 is configured such that it automatically distributes the force load evenly between the condyles/collaterals.

FIG. 6 depicts surgeon 21 just finishing the application of increasing force to the medial collateral ligament, such that monitor 28 lists a force of 25 lbs. on each ligament. The monitor indicates that the knee suffers a vams deformity of 5 degrees and instructs the surgeon to "release" the MCL, or medial collateral ligament. Since the software indicates a varus angle, surgeon 21 must address the soft tissue accordingly by performing a soft tissue release. To perform this release, the tensor is removed from the leg.

Figure 7:
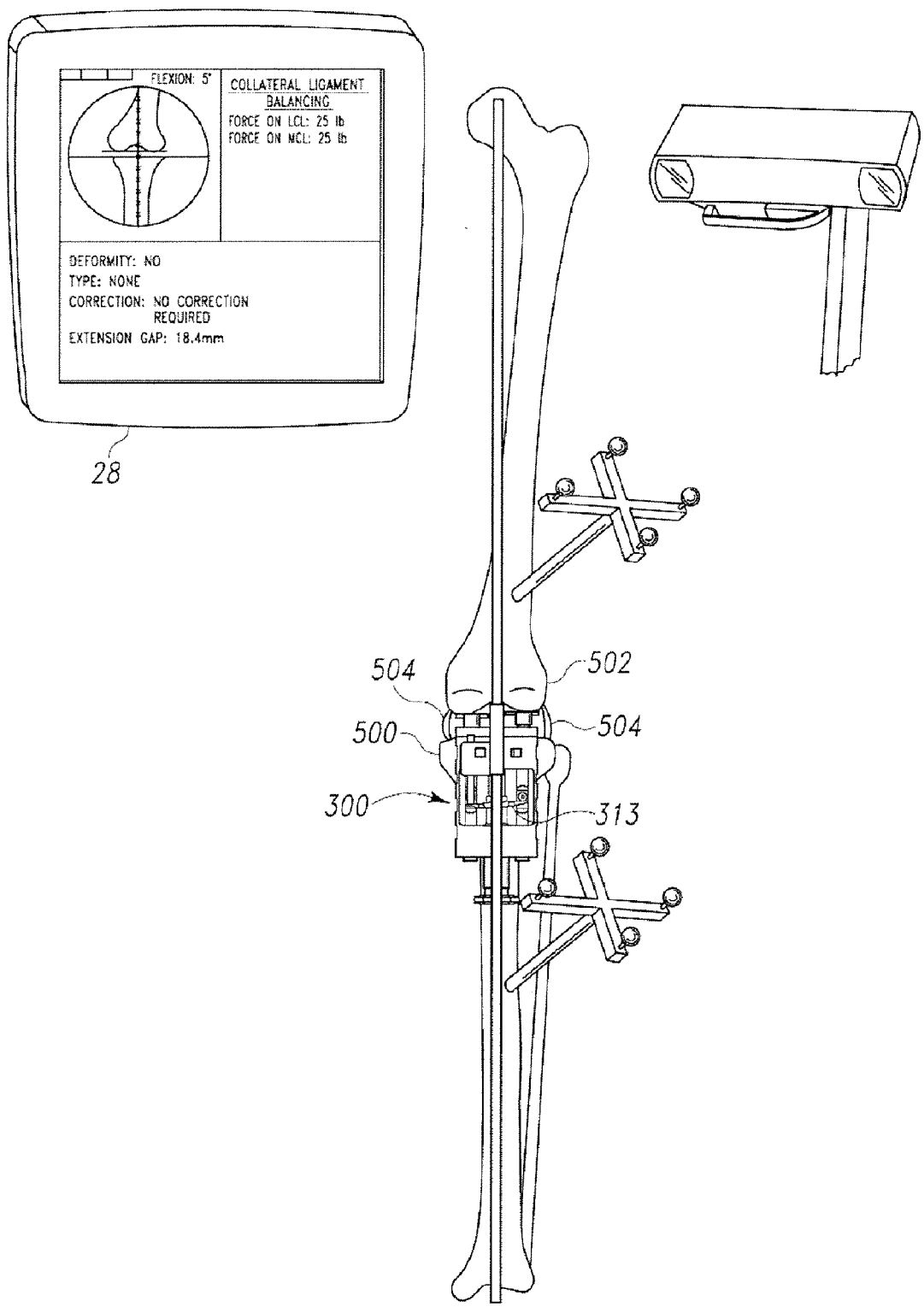

Releasing the MCL can be accomplished by conventional means, typically involving cutting a part of the ligament to extend its length. After the MCL is released, the tensor is replaced and the upper leg alignment checked again. It should be understood and appreciated that the releasing of soft tissue is an iterative process and may be required more than once before completed. As such, the force of the tensor is once again adjusted to provide equal forces to both ligaments. As shown in FIG. 7, monitor 28 indicates that the force exerted on the ligaments is the same and the varus deformity has been corrected. Once proper balance has been achieved, the extension gap is next captured using the computer s software.

Figure 8:
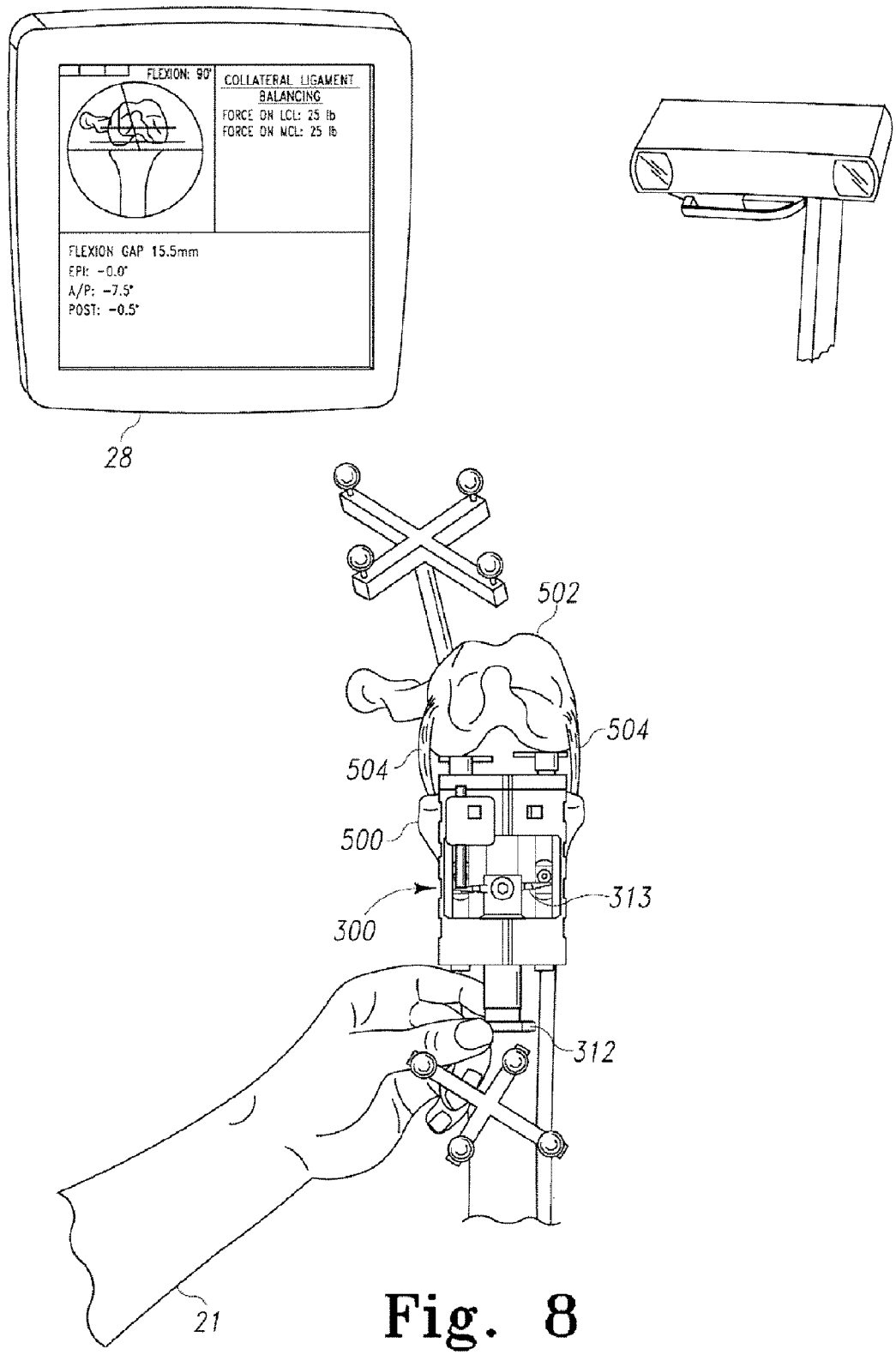

Next, as shown in FIG. 8, the surgeon moves the patient's leg into 90 degree flexion and again performs soft tissue balancing. With the knee positioned at 90 degrees, the tensor is positioned such that the tibia engaging-member is placed on the resected tibial plateau and the femoral engaging-members under the posterior condyles. The operating dial 312 is turned until appropriate tension is achieved (e.g., 20-30 lbs.). While maintaining the knee positioned at 90 degrees and the tensor still in place, the femoral rotation of the knee is assessed by checking and comparing the values of the epicondylar axis, A/P axis, and Posterior condylar axis displayed by the software. Once proper balance has been achieved, the extension gap is once again captured using the computer's software.

Figure 9:
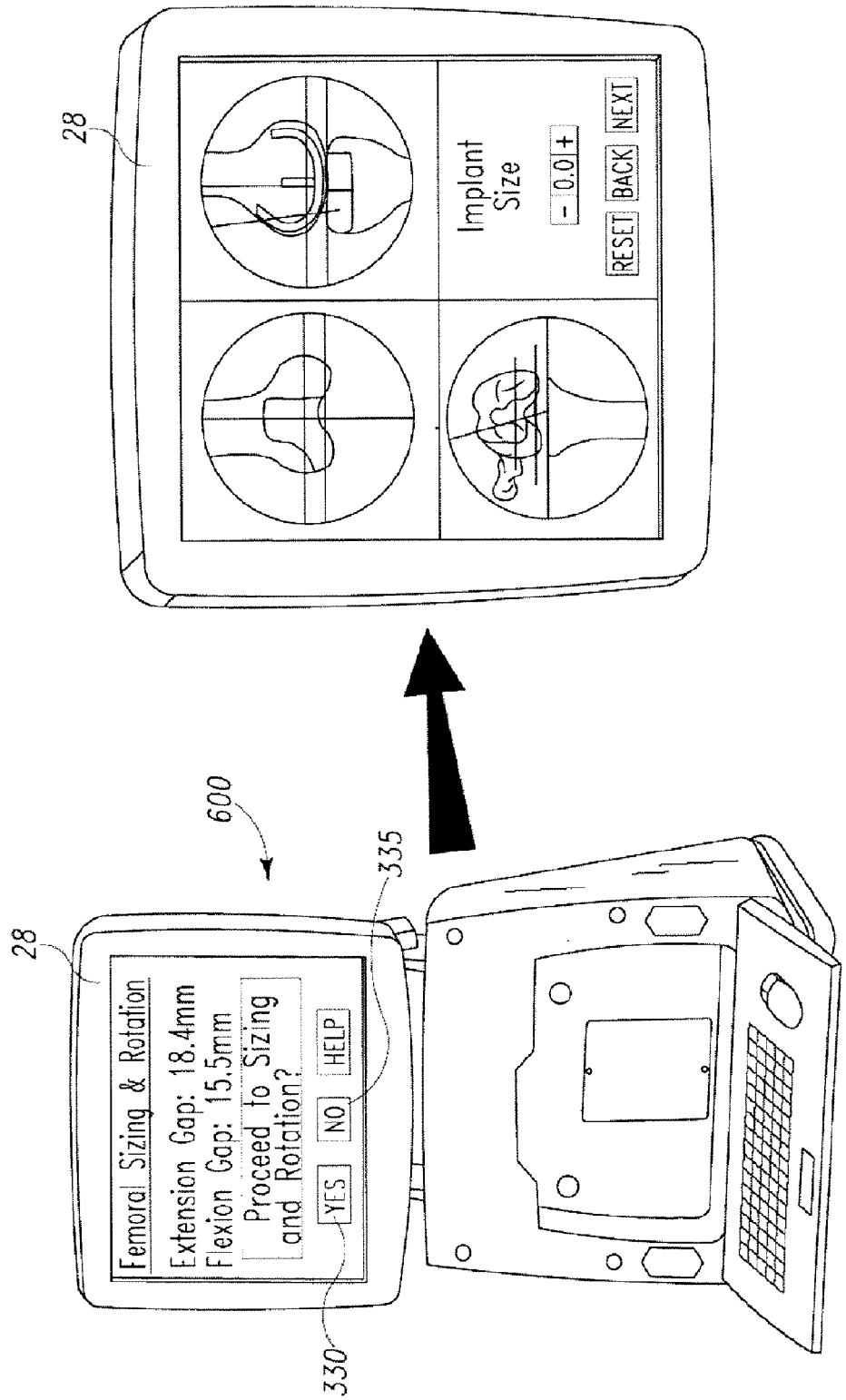

As shown in FIG. 9, computer system 600 is utilized to establish femoral sizing and rotation. The software will position the posterior and distal cuts and the rotation of the implant so that the flexion and extension gaps are appropriately balanced. In the exemplary example shown in FIG. 9, the extension gap is 18.4 mm and the flexion gap 15.5 mm. If this information is appropriate, such that the gaps are deemed balanced, the surgeon will proceed to implant sizing by selecting the "yes" button 330 on monitor 28. If the gaps are deemed not to be balanced, however, the surgeon can instead select the "no" button 335 on monitor 28 and repeat the balancing process as described above. For instance, the leg can be returned to extension and the tensor reinserted to apply an equal amount of force on the MCL and LCL. Once the ligaments are balanced and the femur is held in place, the location of the anterior femoral condyle cuts are chosen so that the extension and flexion gaps are balanced. As can now be appreciated, the tensor has been used to sufficiently balance the extension and flexion gaps such that when the implant is installed, it should remain stable as the knee is moved from extension to flexion.

Figure 10:
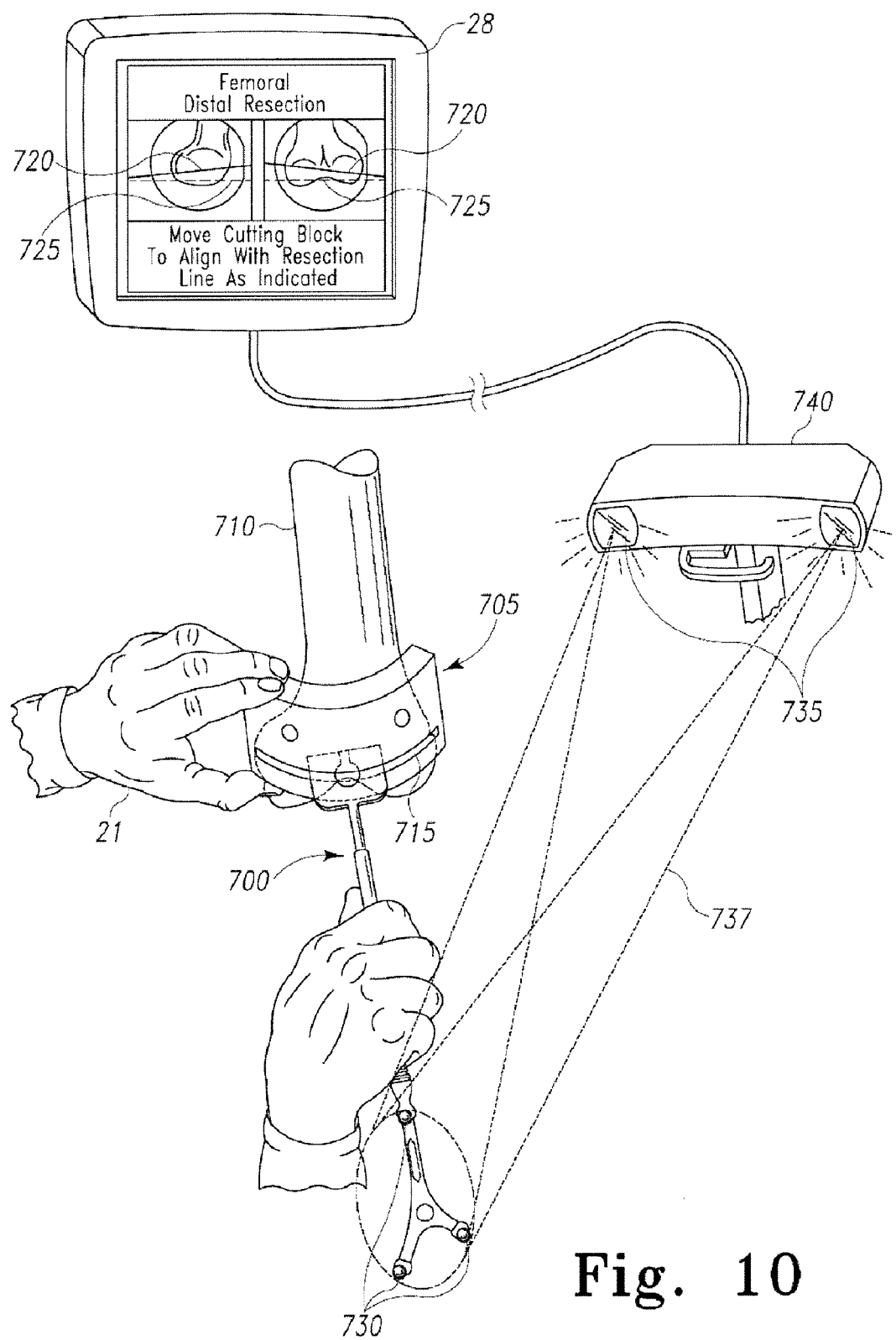

As shown in FIG. 10, before installing the implant, surgeon 21 uses spatula probe 700 to place cutting block 705 along the femur 710 to perform a distal resection. To perform this distal resection, computer monitor 28 guides surgeon 21 as the block is positioned on the femur. By referencing computer monitor 28, surgeon 21 can determine when cutting slot 715 (represented by line 720 on monitor 28) is aligned with the resection cutting plane 725. To accomplish this, markers 730 on spatula probe 700 are tracked by cameras 735 of optical locator 740, which are configured to determine the positions of the markers in space by using triangulation methods (see optical path represented by dashed lines 737). One suitable mechanism for adjusting a cutting block to cut a bone along a resection plane is disclosed in U.S. patent application Ser. No. 11/626,976, entitled Surgical Instrument, filed Jan. 25, 2007, the disclosure of which is hereby incorporated by reference in its entirety.

While the above illustrated embodiment describes using a tensor during a knee ligament distraction procedure, it should be appreciated that the exemplary tensors disclosed herein may also be used to perform various other bone distraction procedures. For instance, the tensor may also be used to distract two or more bones of the spine. According to this illustration, the first and second bone engaging members are respectively adapted to engage first and second vertebral bodies or discs within the spinal column.

Moreover, while the present teachings describe a means for forcibly distracting or moving bony structures or vertebrae with a spring based force-applying mechanism that is configured to forcibly distract such structures with bone engaging members engaged thereto, one of skill in the art would readily recognize several alternate means for applying a predetermined force to the bone engaging members could also be used in accordance with the present teachings. For instance, such other means include, but are not limited to, pneumatic devices, gas cylinders, magnets and/or various other spring arrangements and the like. As such, the present teachings are not intended to be limiting in nature. Indeed, these teachings contemplate a wide variety of means for distracting bones or ligaments with a tensor device.

Figure 11:
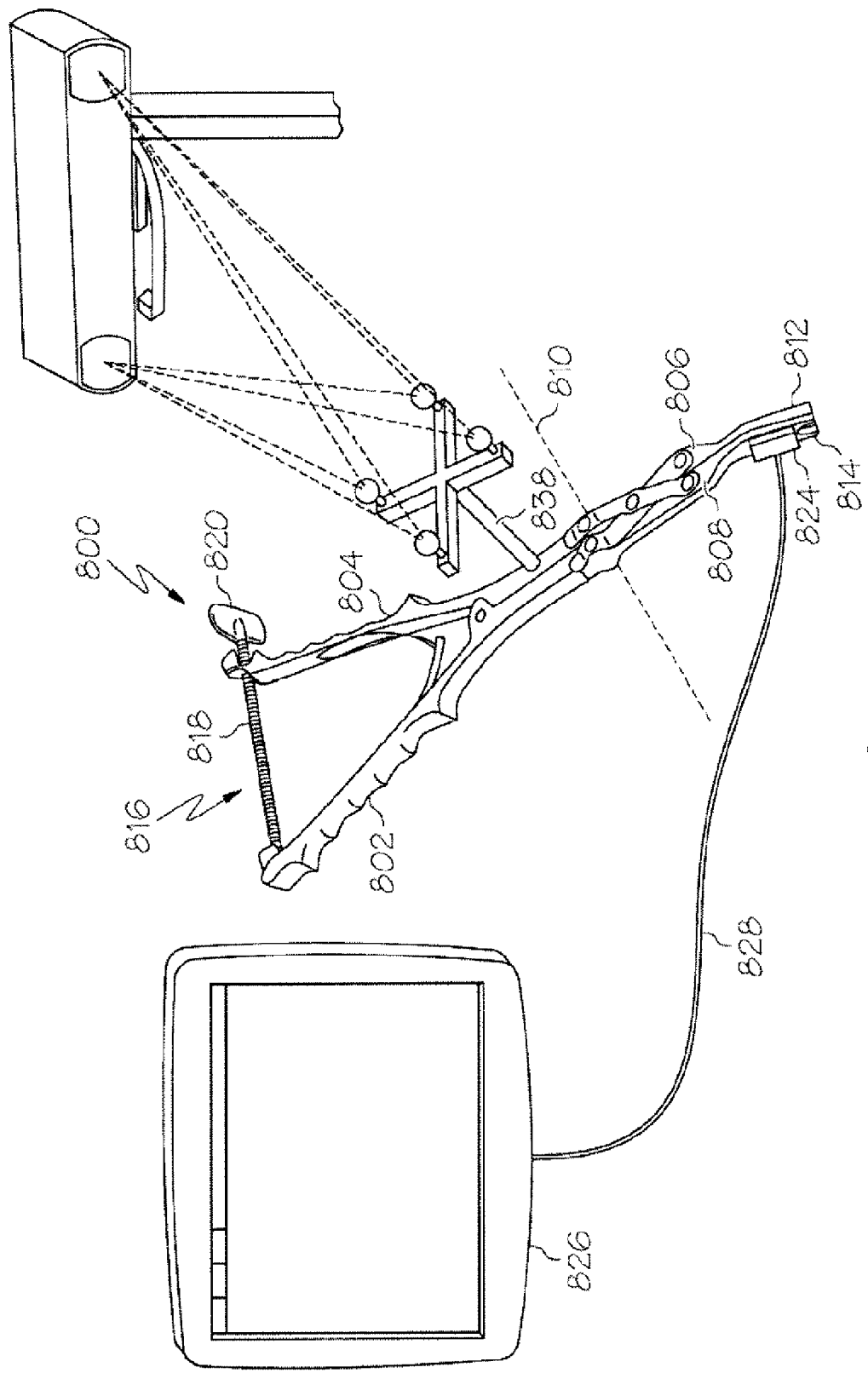
FIG. 11 is a perspective view of an exemplary spinal distractor device in accordance with the present teachings.
Figure 12:
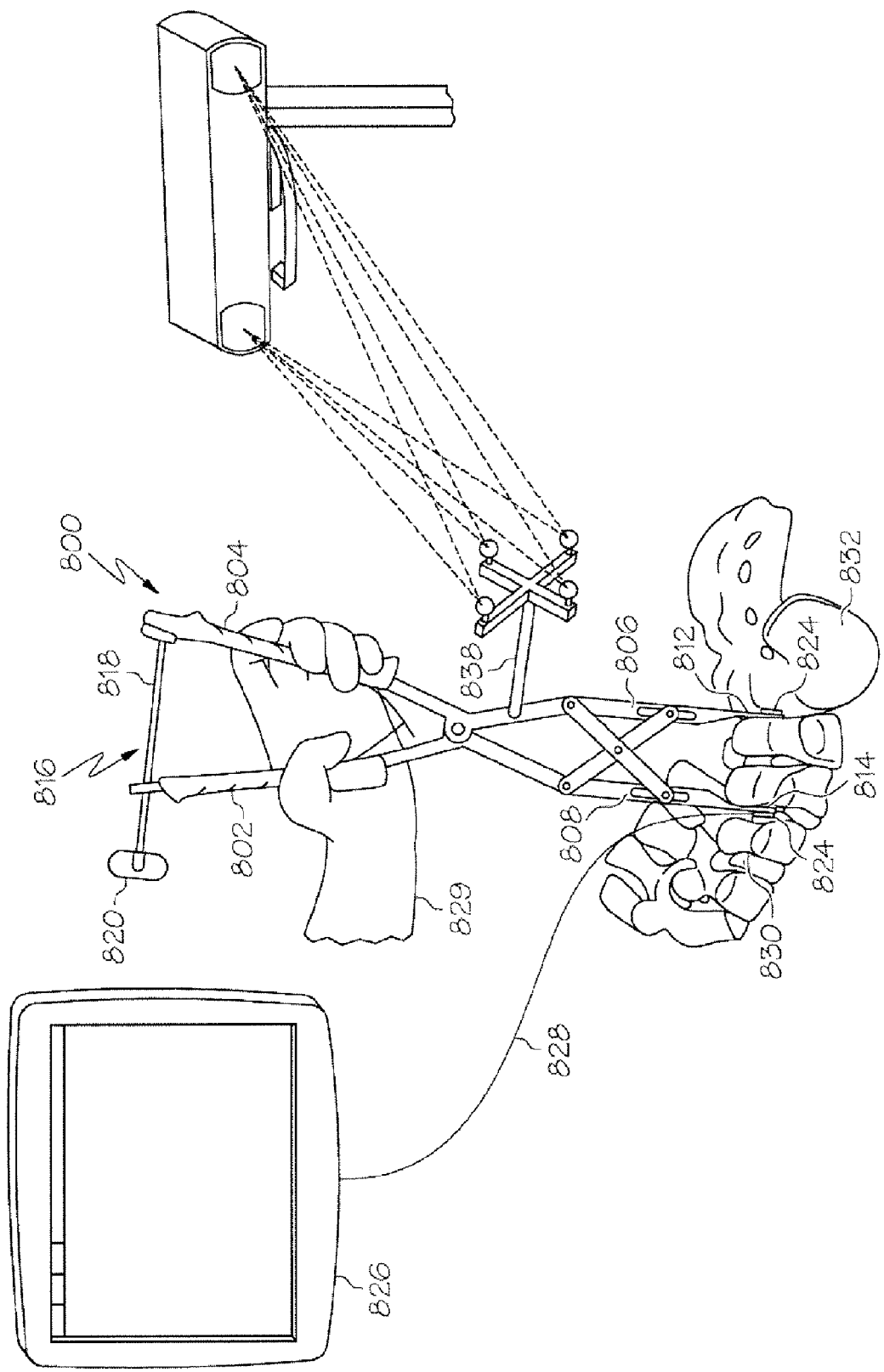
FIG. 12 is a perspective view of the exemplary spinal distractor of FIG. 11 being used to distract a pair of vertebral bodies in a surgical navigation spinal procedure.
Figure 13:
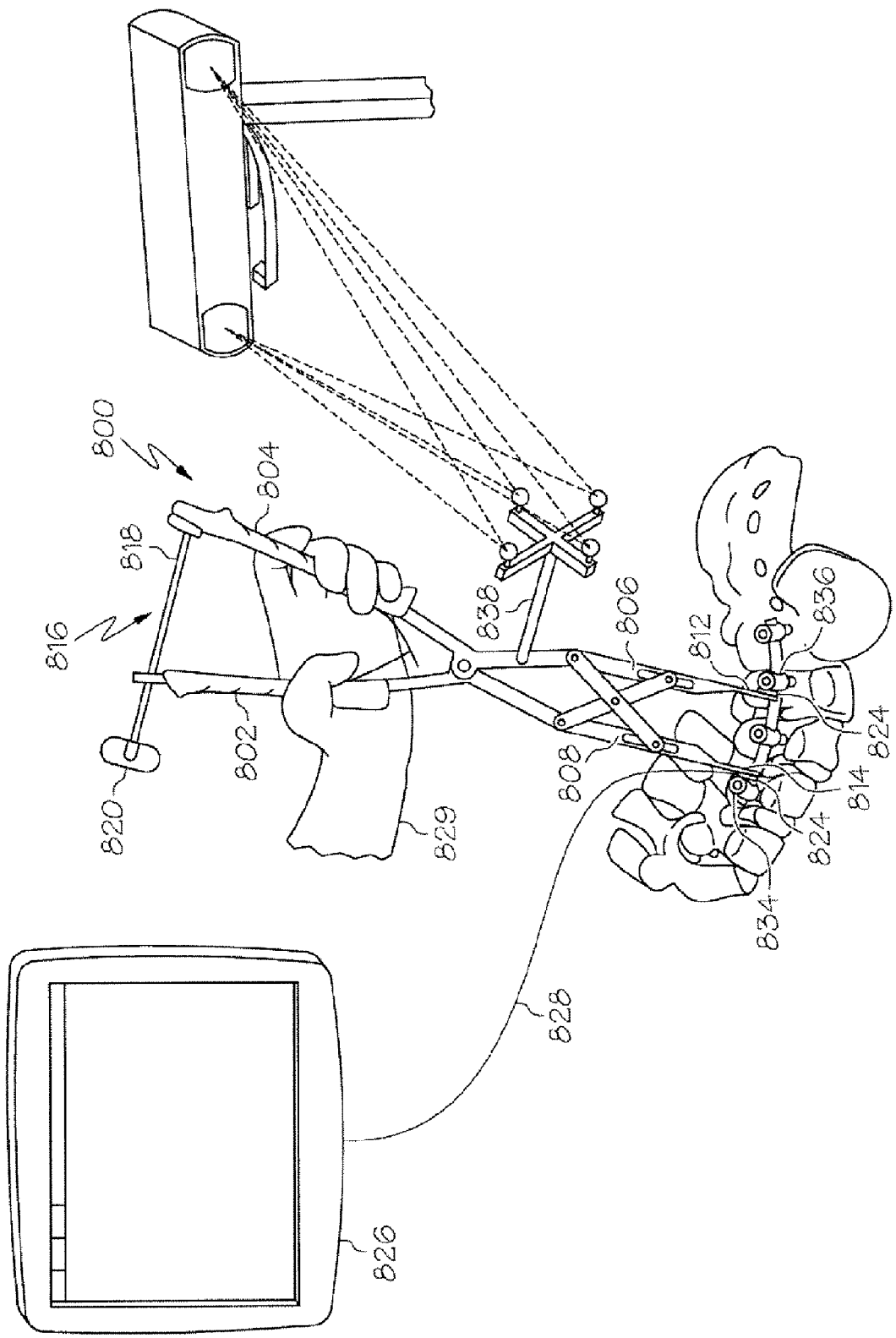
FIG. 13 is a perspective view of the exemplary spinal distractor of FIG. 11 being used to distract a pair of vertebral bodies by way of pedicle screws attached thereto in a surgical navigation spinal procedure.

One illustration of an exemplary spinal tensor or distractor in accordance with the present teachings is shown in FIGS. 11-13. Spinal distractor (tensor) 800 includes a pair of handles 802, 804 that are configured to cause a pair of bone engaging distraction members 806, 808 coupled thereto to move relative to one another substantially along distraction axis 810 during a spinal distraction process. More particularly, handles 802, 804 and bone engaging distraction members 806, 808 are pivotally coupled to each other in a scissors-like (or double scissors-like) configuration such that when the pair of handles are actuated (i.e., squeezed together along distraction axis 810), the distraction members are caused to correspondingly move apart from one another, thereby distracting the vertebral bodies between which the tips 812, 814 of the distraction members are positioned.

Spinal distractor 800 also includes locking mechanism 816 that is provided to maintain a desired spacing of bone engaging distraction members 806, 808 during the spinal distraction procedure. To achieve such a locking arrangement, locking mechanism 816 includes a threaded bolt 818 that is pivotally coupled to handle 804 and slidably passable therethrough. In turn, threaded bolt 818 includes locking nut 820, which is threadably coupled thereto and configured such that its rotation causes the length of bolt 818 positioned between handles 802, 804 to shorten or lengthen as desired. The mechanical operation of such spinal distraction devices is generally known within the bone distraction art and does not require further discussion herein (see for instance, U.S. Pat. Nos. 6,017,342, 6,712,825 and 7,081,118).

To distract spinal members or vertebral bodies, conventional spinal distractors (such as those referenced above) operate on a purely mechanical level. More particularly, the distractor is inserted between the spinal bodies and a force is applied to expand the bodies as needed. The amount of distraction (displacement) and the amount of force that is applied is not determined. However, it is important to not distract the spine too much or apply an unhealthy force to the spine, as it may cause additional injury or an undesired outcome. To minimize these problems, the present teachings provide a means to quantitatively measure both displacement and force during the distraction of two or more spinal members during a distraction procedure.

According to one aspect of the present teachings, spinal distractor 800 is a navigated spinal distractor that can be utilized to measure displacement and/or force. To measure force, transducers 824 are placed on the distractor and are configured to communicate with a computer 826 that is placed within the operating room. More particularly, bone engaging distraction members 806, 808 each include a transducer or load cell device, which is located on the outside portion of its tip 812, 814. These transducers are comprised of a pressure sensitive material or film, such as FlexiForceo Load/Force Sensors and System manufactured by Tekscan, Inc., 307 West First Street. South Boston, Mass. 02127-1309. Transducers 824 are capable of determining the pressure encountered by either one of bone engaging distraction members 806, 808 when they respectively contact a vertebral member (e.g., see reference numerals 830, 832 in FIG. 12) or a hex shoulder of a pedicle screw that affixed to the spine (e.g., see reference numerals 834, 836 in FIG. 13). More particularly, when either one of the bone engaging distraction members 806, 808 come into contact with a vertebral body or associated hardware attached to such vertebral body (e.g., pedicle screw), that distraction member will encounter resistance to movement along distraction axis 810. Because transducers 824 contain a pressure sensitive material, the distraction force is detectable and translatable into a pressure reading that is transmittable to computer 826 via a communication link. In one exemplary embodiment according to the present teachings, the pressure reading is transmitted by the transducers via an infrared transmitter device capable of establishing a communication link with the navigation system. Infrared transmission devices are known in the art and do not need to be discussed in further detail here. In further exemplary embodiments, the communication link is established with the navigation system through a hard-wired connection 828. Whatever means is used to transmit the pressure reading to computer 826, the computer is then configured to record, process and display to the user 829 this force information so that it can be further considered and analyzed as needed.

To measure the displacement of the vertebral bodies 830, 832 or pedicle screws 834, 836 during the distraction process, trackable array 838 is placed on distractor 800. By using a trackable array that is detectable and trackable by the surgical navigation system, the system is able to measure the amount of displacement, including rotation and orientation, of the distractor and therefore the displacing members (e.g., vertebral bodies, pedicle screws etc., as referenced above).

Figure 14:
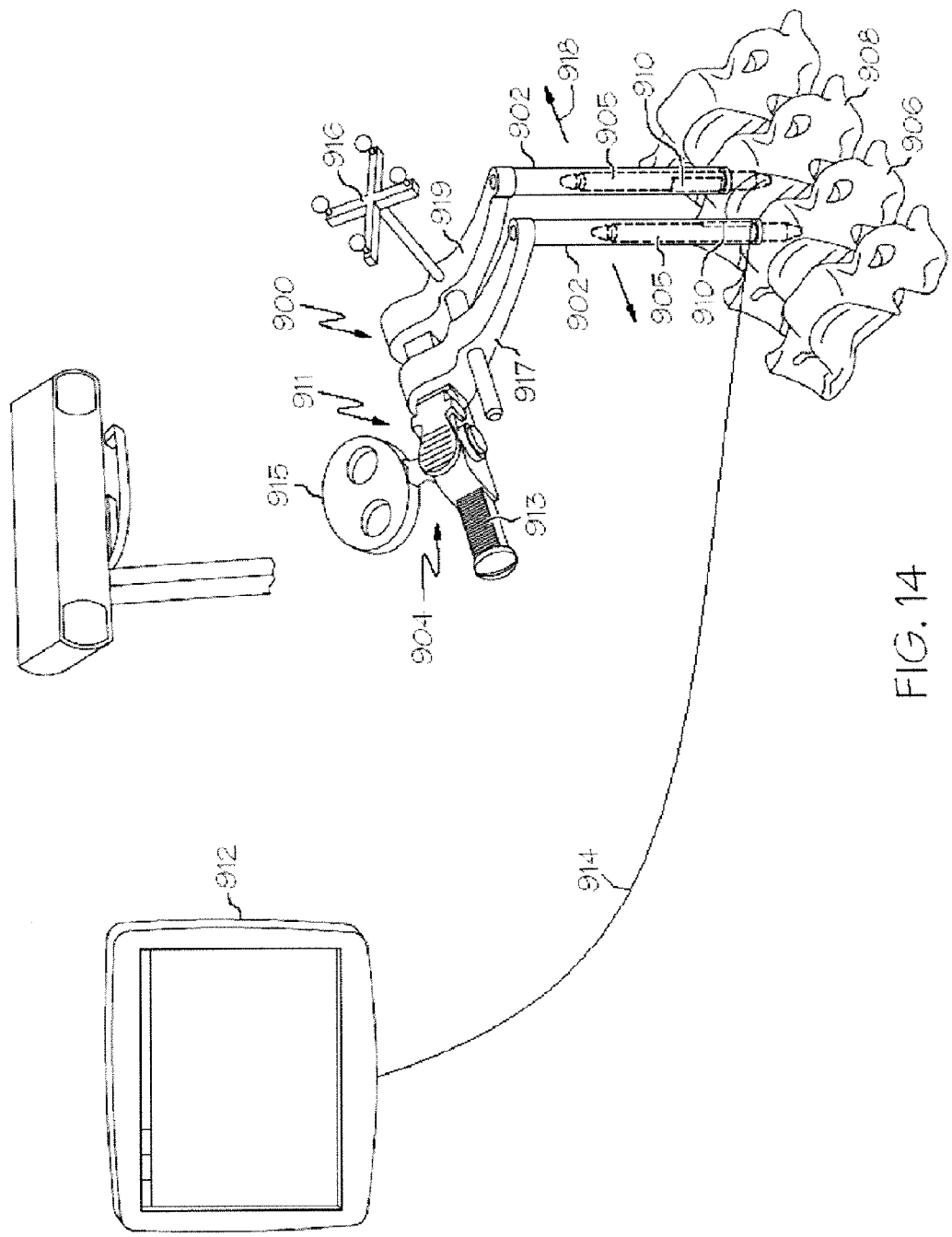
FIG. 14 is a perspective view of another exemplary spinal distractor device in accordance with the present teachings.

Another exemplary embodiment of a navigated spinal distractor in accordance with the present teachings is shown with reference to FIG. 14. Here, distractor 900 includes a pair of bone engaging distraction members 902 and a distraction mechanism 904 for applying and controlling the amount of distraction, if any, desired by the surgeon. The distractor members 902 can be placed over pins 905 drilled into vertebral bodies 906, 908 and then adjusted horizontally with respect to one another to move or distract the vertebral bodies as desired. Spinal distractor 900 also includes locking mechanism 911 that is provided to maintain a desired spacing of distraction members 902, during the spinal distraction procedure. To achieve such a locking arrangement, locking mechanism 911 includes a threaded bolt 913 that is pivotally coupled to distraction arm 917 and slidably passable therethrough. In turn, threaded bolt 913 includes locking nut 915, which is threadably and rotatably coupled thereto and configured such that its rotation causes the length of bolt 913 positioned between distraction arms 917, 919 to shorten or lengthen as desired. The mechanical operation of such spinal distraction device is generally known within the distraction art and can be found for instance, in U.S. Patent Application Publication No. 20060085077, the disclosure of which is incorporated in its entirety by this reference.

To measure the distraction force of distractor 900 during a distraction process, transducers 910 are positioned at the base of pils 905 and configured to communicate with a computer 912 by either a hard-wired 914 or wireless connection. More particularly, pins 905 each include a transducer or load cell device, which is located on the outside portion of its base. These transducers are comprised of a pressure sensitive material or film, such as FlexiForce® Load/Force Sensors and System manufactured by Tekscan, Inc., 307 West First Street. South Boston, Mass. 02127-1309. Transducers 910 are capable of determining the pressure encountered by either one of bone engaging distraction members 902 when they respectively contact the pins that are drilled into vertebral bodies 906, 908. More particularly, when either one of the bone engaging distraction members 902 come into contact with pins 905, that distraction member will encounter resistance to movement along distraction axis 918. Because transducers 910 contain a pressure sensitive material, the distraction force is detectable and translatable into a pressure reading that is transmittable to computer 912 via a communication link. In one exemplary embodiment according to the present teachings, the pressure reading is transmitted by the transducers via an infrared transmitter device capable of establishing a communication link with the navigation system. Infrared transmission devices are known in the art and do not need to be discussed in further detail here. In further exemplary embodiments, the communication link is established with the navigation system through a hard-wired connection 914. Whatever means is used to transmit the pressure reading to computer 912, the computer is then configured to record, process and display to a user this force information so that it can be further considered and analyzed as needed. While this exemplary embodiment illustrates transducers 910 on both pins 905, it should be understood and appreciated herein that the transducers could alternatively be placed on both ends of distraction members 902 of the distractor itself. As such, the present teachings are not intended to be limited herein.

In addition to measuring the force caused by distractor 900 during the distraction process, the amount of displacement between the vertebral bodies 906, 908 may also be measured. To accomplish this measurement, trackable array 916 is placed on distractor 900. By using a trackable array that is detectable and trackable by the surgical navigation system, the system is able to measure the amount of displacement, including rotations and orientations, of the distractor and therefore the displacing members (e.g., vertebral bodies, etc., as referenced above).

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tensor for use with a surgical navigation system, the tensor comprising:

a first bone engaging member engageable with a first bone;
a second bone engaging member engageable with a second bone, the second bone engaging member having a pair of paddles;
a force-applying mechanism positioned along a vertical axis that is centrally disposed between the pair of paddles of the second bone engaging member, the mechanism being configured to forcibly move the first and second bone engaging members relative to one another;
a sensor configured to detect the value of the force applied by the force-applying mechanism, the sensor including a sensing arm having a pressure sensitive material;
a pivot arm coupled to the force-applying mechanism and configured to pivot about a fulcrum point of a central peg, the pivot arm engaging the sensing arm during use of the tensor with a force that is proportional to the force applied by the force-applying mechanism; and
a transmitter for communicating a parameter associated with the tensor to the surgical navigation system.

2. The tensor of claim 1, wherein the parameter comprises force.

3. The tensor of claim 1, wherein the parameter comprises distance.

4. The tensor of claim 3, wherein the distance is taken between the first bone engaging member and the second bone engaging member.

5. The tensor of claim 4, further comprising a display adapted to display the distance between the first bone engaging member and the second bone engaging member.

6. The tensor of claim 1, wherein the first bone engaging member comprises a tibia-engaging member engageable with a tibial plateau and the second bone engaging member comprises a condyle-engaging member engageable with a femoral condyle.

7. The tensor of claim 1, wherein the first bone engaging member comprises a first vertebra-engaging member engageable with a first vertebral body and the second bone engaging member comprises a second vertebra-engaging member engageable with a second vertebral body.

8. The tensor of claim 1, wherein the sensor comprises a transducer.

9. The tensor of claim 1, wherein the transmitter comprises a wireless transmitter.

10. The tensor of claim 1, further comprising a tracking array attachable thereto, the tracking array being detectable and trackable by the surgical navigation system.

11. The tensor of claim 1, wherein the transmitter is releasably attachable to the tensor.

12. A tensor for use with a surgical navigation system, the tensor comprising:
a first bone engaging member engageable with a first bone;
a second bone engaging member engageable with a second bone, the second bone engaging member having a pair of paddles;
a force-applying mechanism positioned along a vertical axis that is centrally disposed between the pair of paddles of the second bone engaging member, the mechanism being configured to forcibly move the first and second bone engaging members relative to one another;
a pivot arm coupled to the force-applying mechanism and configured to pivot about a fulcrum point of a central peg; and
a transmitter for communicating the distance between the first bone engaging member and the second bone engaging member to the surgical navigation system.

13. The tensor of claim 12, further comprising a sensor configured to detect the value of the force applied by the force-applying mechanism.

14. The tensor of claim 13, wherein the transmitter is further configured to transmit the detected force value to the surgical navigation system.

15. The tensor of claim 13, wherein the sensor comprises a transducer.

16. The tensor of claim 12, wherein the first bone engaging member comprises a tibia-engaging member engageable with a tibial plateau and the second bone engaging member comprises a condyle-engaging member engageable with a femoral condyle.

17. The tensor of claim 12, wherein the first bone engaging member comprises a first vertebra-engaging member engageable with a first vertebral body and the second bone engaging member comprises a second vertebra-engaging member engageable with a second vertebral body.

18. The tensor of claim 12, wherein the transmitter comprises a wireless transmitter.

19. The tensor of claim 12, wherein the transmitter is releasably attachable to the tensor.

20. The tensor of claim 13, wherein the sensor comprises a sensing arm that includes a pressure sensitive material.

21. The tensor of claim 20, wherein the pivot arm engages the sensing arm during use of the tensor with a force that is proportional to the force applied by the force-applying mechanism.

22. The tensor of claim 1, wherein the force-applying mechanism is a single rotatable dial that is centrally positioned along the vertical axis.

23. The tensor of claim 12, wherein the force-applying mechanism is a single rotatable dial that is centrally positioned along the vertical axis.

* * * * *